(12) United States Patent
Lorang et al.

(10) Patent No.: US 10,709,577 B2
(45) Date of Patent: *Jul. 14, 2020

(54) GRAFT MATERIAL INJECTOR SYSTEM AND METHOD

(71) Applicant: Benvenue Medical, Inc., Santa Clara, CA (US)

(72) Inventors: Douglas M. Lorang, San Jose, CA (US); Jeffrey L. Emery, Emerald Hills, CA (US); Andrew Huffmaster, Newark, CA (US); Jarrod W. Taylor, San Gabriel, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 198 days.

This patent is subject to a terminal disclaimer.

(21) Appl. No.: 16/021,574

(22) Filed: Jun. 28, 2018

(65) Prior Publication Data
US 2018/0303630 A1 Oct. 25, 2018

Related U.S. Application Data

(62) Division of application No. 15/018,326, filed on Feb. 8, 2016, now Pat. No. 10,022,243.

(60) Provisional application No. 62/112,969, filed on Feb. 6, 2015.

(51) Int. Cl.
*A61F 2/46* (2006.01)
*A61B 17/88* (2006.01)

(52) U.S. Cl.
CPC ......... *A61F 2/4601* (2013.01); *A61B 17/8811* (2013.01); *A61B 17/8825* (2013.01); *A61B 17/8852* (2013.01); *A61F 2002/4627* (2013.01)

(58) Field of Classification Search
CPC A61B 17/8811; A61B 17/8825; A61F 2/4601
See application file for complete search history.

(56) References Cited

U.S. PATENT DOCUMENTS

| | | | | |
|---|---|---|---|---|
| 5,718,707 A * | 2/1998 | Mikhail | ............... | A61F 2/4601 606/94 |
| 6,019,765 A * | 2/2000 | Thornhill | ............... | A61F 2/4601 606/94 |
| 6,059,829 A * | 5/2000 | Schlapfer | ............... | A61F 2/4601 623/17.16 |
| 6,245,072 B1 * | 6/2001 | Zdeblick | ............... | A61F 2/4601 606/914 |
| 8,685,031 B2 | 4/2014 | Kleiner | | |
| 8,906,028 B2 | 12/2014 | Kleiner | | |
| 2012/0136442 A1 * | 5/2012 | Kleiner | ............... | A61F 2/4455 623/17.11 |

FOREIGN PATENT DOCUMENTS

| | | |
|---|---|---|
| WO | WO 2012/048187 A2 | 4/2012 |
| WO | WO 2012/178018 A2 | 12/2012 |
| WO | WO 2014/158680 A1 | 10/2014 |

* cited by examiner

Primary Examiner — Christian A Sevilla
(74) Attorney, Agent, or Firm — Cook Alex Ltd.

(57) ABSTRACT

A graft material injector device and method are disclosed. The injector device includes an elongated injector tube and a side loading aperture for receiving graft material. A graft material loader and a cover for the side loading aperture may optionally be included.

12 Claims, 6 Drawing Sheets

FIG. 15

GRAFT MATERIAL INJECTOR SYSTEM AND METHOD

This application is a division of U.S. patent application Ser. No. 15/018,326, filed on Feb. 8, 2016, which claims priority to and the benefit of U.S. Provisional Application No. 62/112,969, filed Feb. 6, 2015, both of which are hereby incorporated herein by reference.

FIELD OF THE DISCLOSURE

The present invention pertains to devices for minimally invasive procedures in the field of orthopedic surgery and more particularly to deployment of bone graft material into the disc space during a fusion procedure.

BACKGROUND

A major cause of chronic, and often disabling, back pain is disruption or degeneration of an intervertebral disc. The spine is comprised of bony vertebrae separated by intervertebral discs. Each intervertebral disc connects adjacent vertebrae and forms a form of joint that allows movement of the vertebral column. An intervertebral disc is generally divided into two regions: the nucleus pulposus and the annulus fibrosus. The nucleus pulposus is a gelatinous-like tissue that lies at the center of the disc and provides a cushion between adjacent vertebrae. The annulus is made up of collagen fibers that form concentric lamellae that surround and contain the nucleus pulposus.

There are many causes of disruption and degeneration of intervertebral discs, which can be broadly categorized as mechanical, genetic and biochemical. Mechanical damage includes herniation in which a portion of the nucleus pulposus projects through a fissure or tear in the annulus fibrosus. Genetic and biochemical causes usually result from changes in the biochemical processes of a disc. Such changes can be attributed to genetic disorders or environmental influences. Degenerative disc condition is commonly caused by a change in the biochemical process of an intervertebral disc. Such degeneration is a progressive process that usually begins with a decrease in the ability of the nucleus pulposus to absorb water. With a loss of water content, the nucleus becomes dehydrated, resulting in a decrease of internal disc hydraulic pressure, and ultimately to a loss of disc height. This loss of disc height can cause the annulus to buckle, eventually resulting in annular fissures and ruptures. Herniation occurs when a rupture leads to protrusion of the nucleus pulposus through the annulus.

Furthermore, disc height plays an important role in the functionality of the intervertebral disc and spinal column, and changes in disc height can have both local and wider effects. On the local (or cellular) level, decreased disc height may result in increased pressure in the nucleus pulposus, which can lead to a decrease in normal cell operation and an increase in cell death and disintegration. In addition, increases in intra-discal pressure may create an unfavorable environment for fluid transfer into the disc, which can cause a further decrease in disc height.

Decreased disc height also results in significant changes in the larger mechanical stability of the spine. With decreasing height of the disc, the facet joints bear increasing loads and may undergo hypertrophy and degeneration. Decreased stiffness of the spinal column and increased range of motion resulting from loss of disc height can lead to further instability of the spine, as well as back pain.

Several disc defects may be treated by implantation of a prosthetic into the nuclear space of the intervertebral disc. Some procedures that may include insertion of a prosthetic into the disc are spinal fusion and disc repair and replacement. Prior to implantation of most prostheses, a discectomy is often performed to prepare the nuclear space for implantation of the prosthetic and, when spinal fusion is desired, to facilitate bony fusion between the vertebral bodies. Some implantation procedures may require a total discectomy in which the majority (and usually all) of the volume of the nucleus pulposus is removed. Others may require a partial discectomy in which only a portion of the nucleus pulposus is removed.

Traditionally, when a fusion is the desired treatment option, there are several approaches to access the disc space and position an implant to regain the proper disc height. For a typical posterior surgical approach, an incision is made through the back of a patient and access to the disc space is achieved. Manual instruments are used and inserted through the access to the intervertebral disc requiring treatment. The curettes and rongeurs are used to cut, tear, and remove nucleus pulposus tissue one piece at a time, and the rasps are utilized to roughen or scrape the endplates of adjacent vertebrae. Other options have been disclosed previously to provide a more accurate and minimally invasive disectomy such as disclosure "Disc preparation tools and methods using the same" U.S. Application Ser. No. 62/021,960, filed Jul. 8, 2014.

Once the disc has been removed, the implantation of the intervertebral implant device can be achieved. Such devices and methods have also been previously disclosed in application "Device for treating the Spine" U.S. application Ser. No. 12/035,298, filed Feb. 21, 2008, and more particularly, in application "Spinal fusion implants and devices and methods for deploying such implants" U.S. application Ser. No. 13/803,322, filed Mar. 14, 2013 and incorporated by reference herein.

A further component needed in the fusion process to create bony fusion between the two vertebral bodies and that is bone graft material or bone filler material (both of which are generally referred to herein as graft material). Such material will favor the creation of a bony bridge that spans across the implant and connects the inferior (lower) cartilaginous endplate of the superior (upper) vertebral body to the superior (upper) cartilaginous endplate of the inferior (lower) vertebral body.

Traditionally, the graft material (bone graft material and/or bone filler material) is positioned into the implant, such as a cage, prior to insertion into the disc space and due to this process cannot be fully optimized for best endplate to endplate contact.

In addition, previous graft delivery systems are back-loading, such that the graft material must be advanced a great distance through the barrel before it is extruded into the delivery site. More work (force applied over a greater distance) is therefore required to achieve this successfully, and often the nature of the graft material may cause significant binding when pushed over longer distances, rendering the device unusuable.

Minimally invasive spinal surgery requires that all surgical tools be as small as possible to minimize tissue trauma and exposure to the surgical site. Tools to deliver bone graft that have a delivery diameter of 10 mm or less are highly susceptible to requiring large forces to deliver the bone graft material or, in the worst case, may seize entirely because of the high resistance developed when pushing materials of large, irregular grain size like autograft bone graft material.

This susceptibility to seizing is aggravated by the length over which the graft must be delivered down the tool, which is typically 6 or more inches if the material is loaded at the most proximal tube position and pushed all the way to the delivery site.

Typical bone graft tools incorporate a proximal funnel, a long tube length, and a manual tamp that requires the user to tap to deliver the graft to the site. Large bone chips loaded into the tube chamber can contribute significantly to delivery resistance. To overcome the resistance, the outer diameter of the delivery tube is often quite large (>10 mm). Further, the loading of these long-bored funnels must be done at the surgical site, lest the material fall out at an undesirable location. Thus, this requires the primary surgeon to load and tamp the graft material into place.

There continues to be a need for further development and advancement in this field. For instance, in disclosure PCT publication WO 2014/158680 (incorporated by reference herein) FIG. 32 shows a cannula that extends thru the side wall of an implant device to introduce the bone graft material but no specific device or method is disclosed.

SUMMARY

In accordance with one aspect of the present subject matter, a bone graft material injector is provided comprising: an injector device including an elongated injector tube, an internal injector tube lumen extending through the injector tube and having a longitudinal axis, a distal injection aperture communicating with the lumen and a side loading aperture for receiving a quantity of graft material into axial alignment with the lumen axis; and a graft material loader cooperatively engageable with the side loading aperture and adapted to load a selected quantity of graft material into axial alignment with the axis of the injector tube lumen.

In another aspect a graft material injector device is provided comprising: an elongated injector tube including an internal lumen; a distal injection aperture communicating with the injector tube internal lumen and a side loading aperture communicating with the lumen; and a cover associated with the side loading aperture and movable between a position substantially closing the side loading aperture and a position substantially opening the side loading aperture for loading graft material into the internal lumen.

In a further aspect, as a graft material injector is provided comprising: elongated injector assembly comprising an inner elongated injector tube and outer elongated cannula tube, the injector tube including a proximal end portion and a distal end portion with a lumen extending therethrough; a handle secured to the proximal end portion of the injector tube; an injection aperture in the distal end portion of the injector tube; and an elongated side loading aperture in the injector tube proximal of the injection aperture. The outer cannula is sized to movably receive the injector tube therein, and the cannula and tube are relatively movable between a position in which the cannula substantially covers the side loading aperture to close the side loading aperture and a position in which the cannula does not substantially cover the side loading aperture to open the side-loading aperture for receiving graft material into the injector tube lumen. The handle includes an actuator engaged with the cannula for sliding the cannula between the positions substantially covering the side loading aperture and not substantially covering the side loading aperture.

In accordance with another aspect, a method is provided for injecting graft material into a spine disc surgery site employing any of the above apparatus. More specifically, a method of injecting graft material into cooperative association with a spine disc implant is provided comprising: introducing graft material into axial alignment with an injector tube lumen through a side loading aperture; closing the side loading aperture; positioning the distal end of the tube into the desired position with respect to the implant; and moving a push rod through the lumen, thereby applying force to the graft material to force it out the injection aperture and into association with the implant.

These and other aspects are found in the drawings hereof and the detailed description below.

DETAILED DESCRIPTION OF DRAWINGS

DETAILED DESCRIPTION

Figures 1, 2:
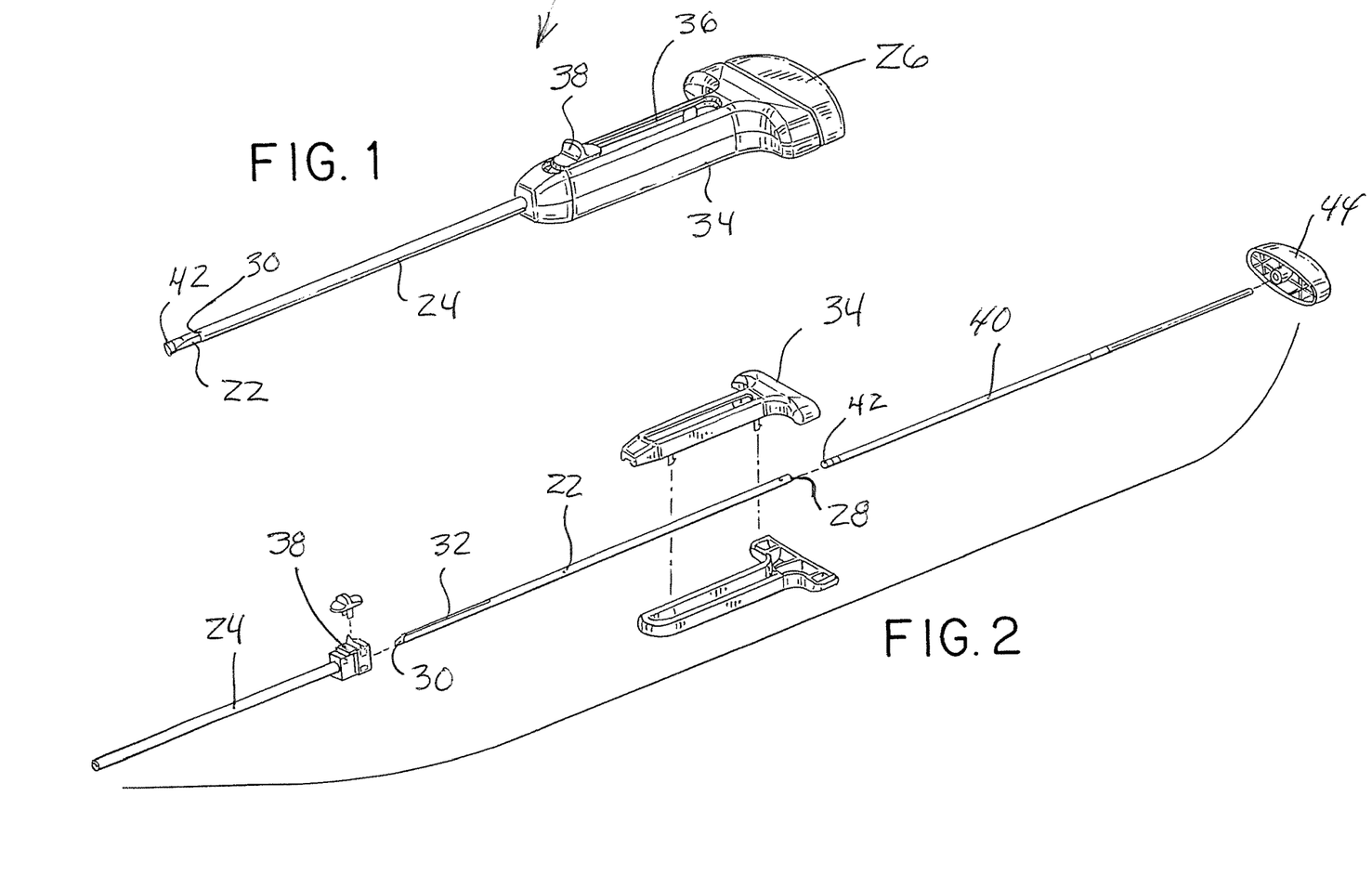
FIG. 1 is a perspective view that shows one embodiment of a graft material injector device.
FIG. 2 shows an exploded perspective view of graft injector device of FIG. 1.

FIGS. 1 and 2 depict one non-limiting example of a fusion graft material injection assembly or device generally at 20 embodying certain aspects of the present subject matter. The illustrated injection device 20 includes an elongated injector tube 22, that is axially relatively movable with respect to an outer cannula 24, and a pusher 26 that is advancable through the injector tube. The elongated injector tube has an internal lumen extending between a proximal end opening 28 and a distal end opening 30. A side loading aperture illustrated in the form of an elongated slot 32 in the wall of the injector tube, is located preferably but not exclusively in the distal end portion of the tube proximal of the distal end opening 26. The distal tip of the injector tube could be square cut or beveled to facilitate entry into tighter locations. A beveled tip could be oriented with respect to injector tube handle 34 to be indicative to the surgeon of bevel opening direction. The tip could also have longitudinally oriented slits that could allow the tube to collapse into tighter spaces and then expand when graft material and pusher 26 are advanced through the injector tube lumen. Alternatively, the tip of the injector tube could be made of soft, pliable, non-atraumatic material. The injector tube, cannula and/or pusher may be made of any suitable material, such as stainless steel or rigid plastic.

Handle 34 is attached to the proximal end portion of the injector tube 22 and is ergonomically configured for gripping ease. The handle includes a proximal opening in axial alignment with the injector tube lumen to receive the pusher 26. The illustrated handle includes an axially extending slot 36 that slidably receives an actuator, such as a thumb tab 38, connected to the proximal end of cannula 24. Pusher 26 includes an elongated rod or pin 40 having a closed distal end 42. An ergonomically shaped handle 44 is secured to a proximal end of the rod.

The cannula 24 and injector tube 22 are respectively sized for close fitting but still slidable engagement between the outer surface of the injector tube and the inner lumen surface of the cannula. With this arrangement, the cannula 24 defines, in effect, a cover that is movable relative to the injector tube between (1) a substantially open or uncovered position that exposes the side aperture or elongated slot 32 for loading graft material into the injector tube, and (2) a substantially closed or covered position, where the cannula extends over and covers the slot 32 after graft material has been introduced into the slot.

Similarly, the injector tube lumen and the pusher rod 40 are respectively sized for close fitting but relatively movable engagement. As explained herein, the pusher is used to push against graft material that has been loaded into the injector tube so as to apply force against the graft material and push it out the distal end opening 30 of the injector tube. The relative close fit between the pusher rod 40 and injector tube lumen prevents substantial amounts of graft material from entering the spacing between the pusher rod distal end and the injector tube lumen when the pusher rod is advanced against graft material in the injector tube lumen. The illustrated pusher 26 is configured for slidable moving of the pusher rod 40 within the injector tube lumen. However, the injector device may also be configured with a threaded engagement between the pusher 26 and injector tube or injector tube handle such that rotation of the pusher handle 44, which could be in the form of a knob, advances the pusher rod within and along the injector tube lumen. Threaded engagement may provide greater control of injection rate and/or volume and provide mechanical advantage over a sliding arrangement. As a further alternative, the pusher rod 40 could be significantly smaller than the injector tube lumen, but terminate at a larger distal end such as a flexible, compliant polymeric or low-friction tip that is closely sized relative to the injector tube lumen or in a state of compression therein so as to fully fill the lumen. Still another alternative is for the plunger distal tip to be of metal to provide a stiff rigid member that can be used as a graft material tamp after the material is ejected from the distal end of the injector tube.

While FIGS. 1 and 2 show a graft injection device or assembly 20 with an injector tube 22 having side loading aperture in the form of a single elongated slot 32, the injector tube may have more than one loading aperture, and the aperture(s) may be of any suitable size or shape. Because bone graft material can include bone chips or particles of relatively large size that clog or impede delivery through the injector tube, the side loading aperture may also include or be in the form of a filter mesh or sieve that allows only graft material below a certain size to pass into the injector tube lumen. Such a filter or sieve may take any suitable configuration and may be in the form of pores or slits laser cut through the side wall of the injector tube.

Figures 3, 4:
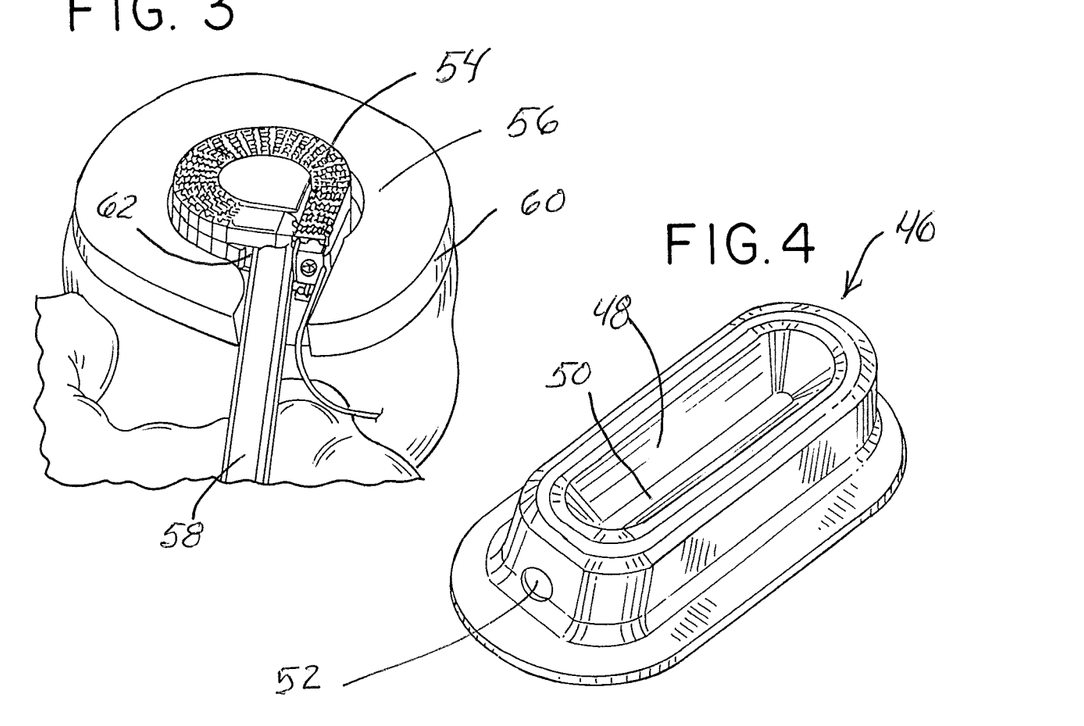
FIG. 3 shows one embodiment of a possible application for the bone graft injector of FIG. 1.
FIG. 4 is a perspective view that shows one embodiment of a potential loading hopper or graft material guide.

In the illustrated embodiment, the graft material device assembly may optionally include a guide or hopper 46 to assist in introducing graft material into the injector tube. The guide may have any suitable shape. As illustrated in FIG. 4, the guide is in the form of a funnel having a funnel wall 48 inclined toward a funnel outlet 50. More particularly, in this non-exclusive embodiment the guide is elongated and has an elongated outlet substantially the same length at the elongated slot 32 in the injector tube 22. The width of the outlet slot 50 in the guide may be approximately the width of the elongated slot 32 or may have a wider or narrower width. A narrower width may be selected to prevent graft particles exceeding a certain size from entering the injector tube. In this form, the elongated funnel outlet acts as a filter or sieve. Alternatively, a separate filter or sieve structure may be located in the funnel outlet or otherwise mounted in the funnel to filter or sieve the graft material. The size and profile of the guide affords a stable, horizontal loading position for introducing graft material into the injector tube. Variations of these features allow the guide and injector device to be adapted to change the angle of orientation with respect to the user, such as a 30° or 45° angle.

The illustrated guide 40 includes an injector tube guide in the form of an opening or aperture 52 into which the injector tube is inserted for graft material loading purposes. The opening 52 is located so as to cause alignment of the elongated slot 32 in the injector tube 22 with the elongated outlet 50 in the funnel-shaped guide 46 when the injector tube is inserted into the aperture 52. More specifically, when the injector tube is inserted into the aperture 52 of the funnel, the elongated slot 32 and elongated outlet 50 are in registration and contact so that graft material can be forced, typically by manually applied pressure, from the funnel into the injector tube. This provides a selected quantity or bolus of graft material in the injector tube having a length approximately that of the elongated slot 32 and a diameter or cross-sectional size of the injector tube lumen.

Figure 5:
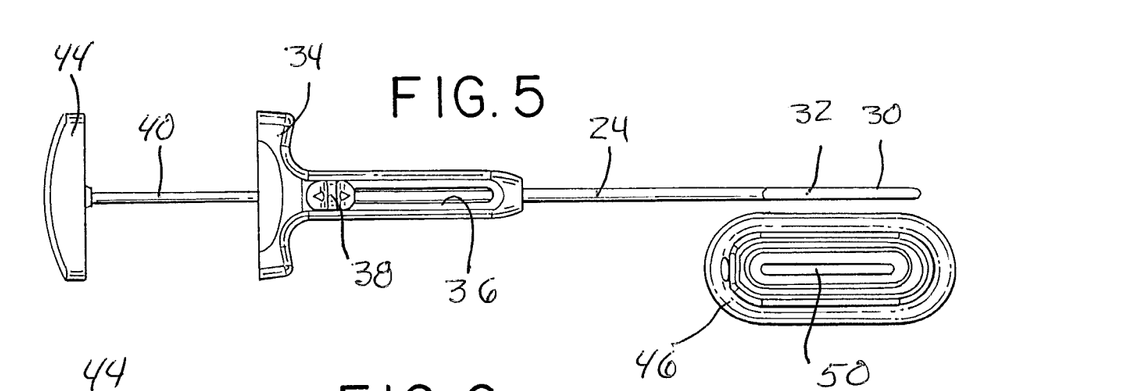
FIG. 5 shows one embodiment of a potential step one of the usage of the device.

Steps for introducing graft material into the injector tube are generally illustrated in FIGS. 5-9. FIG. 5 shows the graft injection assembly in a loading configuration with the pusher 26 withdrawn to a position where the distal end of pusher rod 40 is proximal of the elongated slot 32. Similarly, the thumb tab 38 of the cannula 24 is slid to the proximal end of handle slot 36. In this position, the cannula 24 is retracted to substantially and preferably completely uncover the elongated slot 32 of the injection tube 22.

Figure 6:
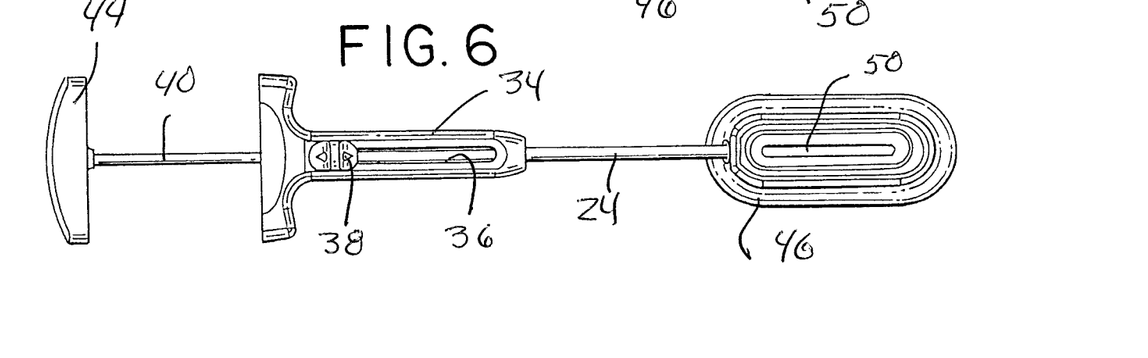
FIG. 6 shows one embodiment of a potential step two of the usage of the device.

FIG. 6 depicts the injector assembly, in the loading configuration of FIG. 5, with the injector tube inserted into opening 52 of guide 46. This positions the elongated slot of the injector tube in registration with the elongated outlet 50 of the funnel shaped guide. (FIG. 7 is essentially similar to FIG. 6.)

Figures 7, 8:
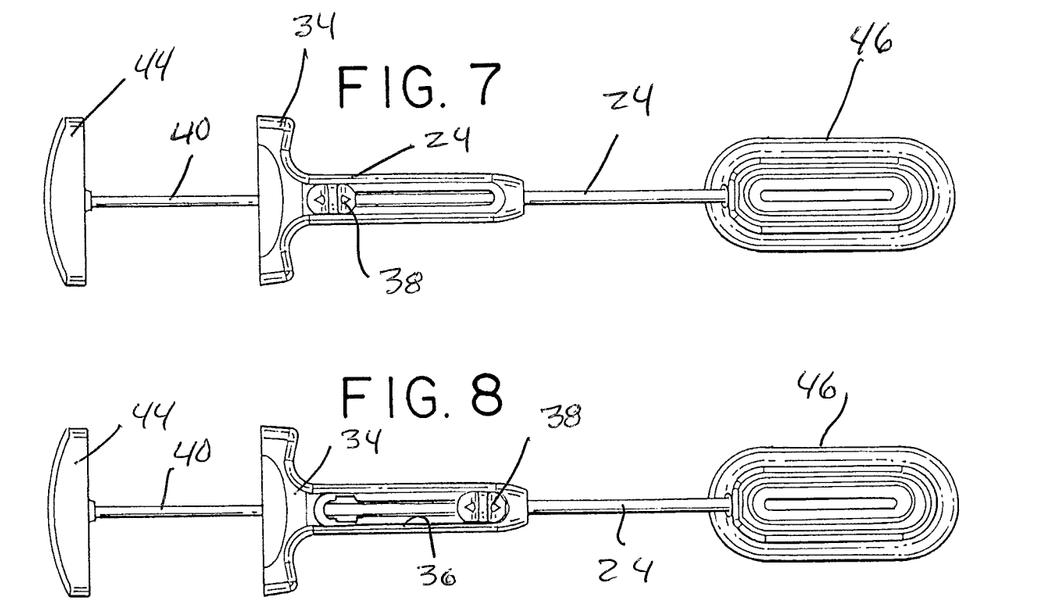
FIG. 7 shows one embodiment of a potential step two of the usage of the device.
FIG. 8 shows one embodiment of a potential step three of the usage of the device.

In the position of FIGS. 6 and 7, graft material may be forced, by manual pressure or tamp, from the funnel shaped guide, through the elongated outlet 50 and elongated injector tube slot 32, into the injector tube lumen, filling it with a selected amount (e.g., about 1 cc) of graft material axially positioned within the lumen.

Figure 9:
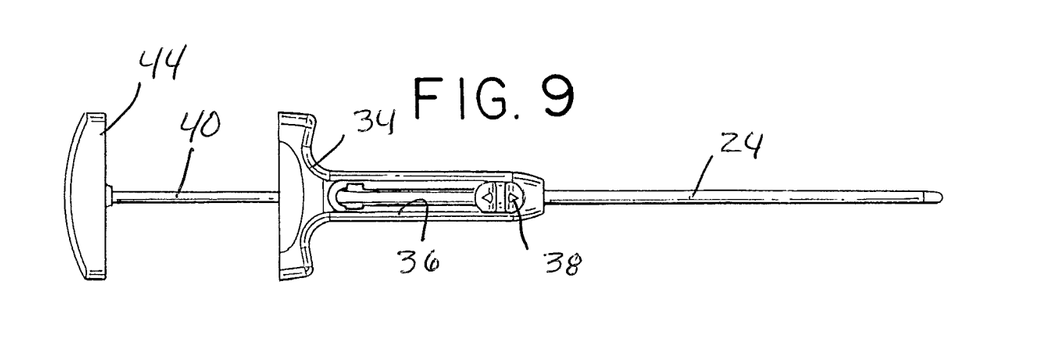
FIG. 9 shows one embodiment of a potential step four of the usage of the device.
Figure 10:
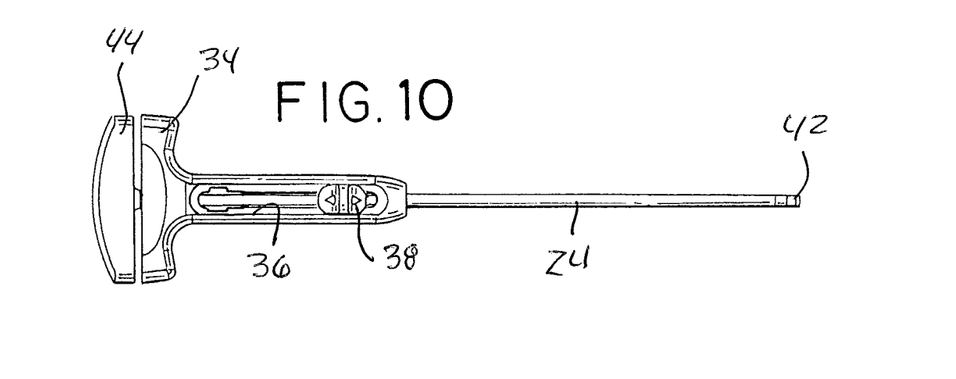
FIG. 10 shows one embodiment of a potential step five of the usage of the device.

The cannula 24 is then moved to the distal position in the handle slot 36, as shown in FIG. 8. This covers and closes the slot, readying the assembly for the next steps. The injector assembly is then withdrawn from the guide 46, with the pusher 26 still in the retracted position, as seen in FIG. 9.

The distal end portion injection assembly is then introduced into the surgical site where the graft material is required. One such surgical site may be the intradiscal space of the human spine. FIG. 3 shows such an exemplary site, with an implant 54 located within a central area of a disc 56, from which the nucleus has been removed in preparation for the procedure. An access tube 58 is shown extending through an access opening in the disc annulus 60 and into a window 62 in the disc implant. The distal end of the injector tube 22 and cannula 24 may be inserted through the access tube or directly into the implant window (without an access tube), requiring only a small access opening in the tissue, such as about 5 mm, that reduces risk of tissue trauma. When suitably located, the pusher 26 is advanced while the injector tube is held fixed. The distal end of the pusher rod 40 engages and pushes the length of graft material along the distal end portion of the injector tube and out the distal end opening 30 into the central space within the implant. The travel of the pusher rod may be configured to optimize or indicate to the user the volume of graft material dispensed or the maximum volume dispensed. Of course, the illustrated implant is but one example, and the fusion graft injection assembly or device as described herein may be used with other forms or types of implants or even without implants if only delivery of graft material to a surgical site is desired. After injection, the assembly 20 may be withdrawn, and the loading and injection procedure repeated until sufficient graft material has been delivered to the surgical site.

Figure 11:
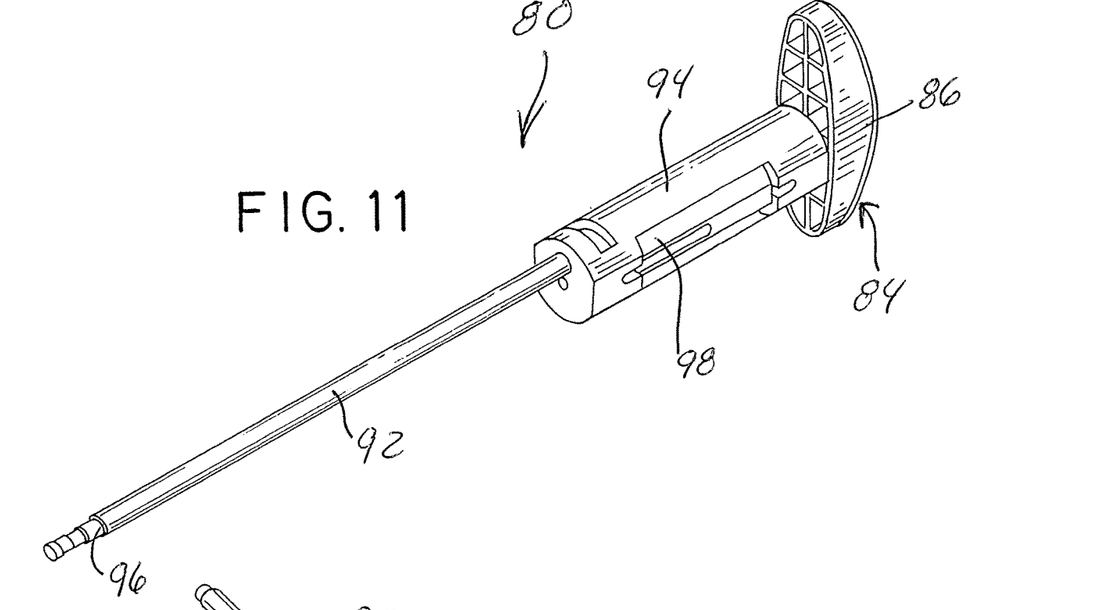
FIG. 11 is a perspective view of another embodiment of a graft material injector device/system.

An alternative embodiment of the fusion graft injection assembly or device is shown in FIGS. 11-15, and generally identified by reference numeral 80 in FIG. 11. As illustrated, the assembly or device 80 includes an injector tube and handle assembly 82 and pusher 84. The pusher 84 is constructed essentially the same as the pusher 26 described earlier, and includes a handle 86 and pusher rod 88, illustrated with a slightly enlarged blunt distal end 90.

The injector tube and handle assembly 82 includes elongated injector tube 92 and a handle or frame 94. In this embodiment the injector tube 92 includes an internal lumen that extends between the handle 94 at the proximal end and a distal end opening 96. The handle 94 has a side loading aperture 98 that is sized to receive a magazine 100 having a plurality of graft material chambers 102.

In the illustrated embodiment, the magazine 100 is illustrated in the form of a rotary cylinder with six graft material chambers disposed around the cylinder and extending through the length of the cylinder so as to be open at each end or through chambers. The cylinder is rotatable within the handle 94 to allow each of the graft material chambers to axially align with the axis of the injector tube lumen in an injection position. The proximal end of the handle 94, as in the prior embodiment, has a proximal opening 104 that is also axially aligned with the injector tube lumen, for receiving the pusher rod 88.

In this arrangement the graft material chambers 102 may be pre-filled with graft material and loaded into the handle 94 side loading opening 98. Rotation of the magazine or cylinder brings one of the chambers into axial alignment with the injector tube lumen, allowing the pusher rod 88 to be advanced through the handle proximal end opening 104, through the aligned graft chamber 102 and through the injector tube 92. In this manner, graft material in the aligned chamber can be pushed by the force of the pusher rod out of the chamber and along the injector tube lumen, exiting from the distal end opening 96 of the injector tube into the desired location at the surgical site. The pusher rod may then be retracted proximal to the magazine 100, which can be rotated to align another graft material chamber with the injector tube lumen and the pusher rod again advanced to push another quantity or bolus of graft material along the injector tube for delivery to the surgical site. This can be repeated as needed to deliver the desired amount of graft material without the need to withdraw the injector tube from the surgical site to refill it.

Although the graft material magazine is illustrated as a cylinder, it may be of any other suitable shape, such as a linear feed arrangement where the graft material chambers are disposed in a side by side relationship for sequential positioning into an aligned injection position or one behind another, if so desired. Also, the magazine may be removable from the handle to allow an emptied magazine to be refilled with graft material or replaced with a full magazine without the need to withdraw the injector tube from the surgical site.

Referring back to the figures, FIG. 11, shows the injection assembly with the magazine 100 received within the handle side loading aperture 98 and the pusher rod 88 advanced fully through the handle, the aligned graft material chamber and the injector tube lumen. The distal end 90 of the pusher rod may be seen extending beyond the distal end of the injector tube, where it may be used to tamp the graft material at the surgical site.

Figure 12:
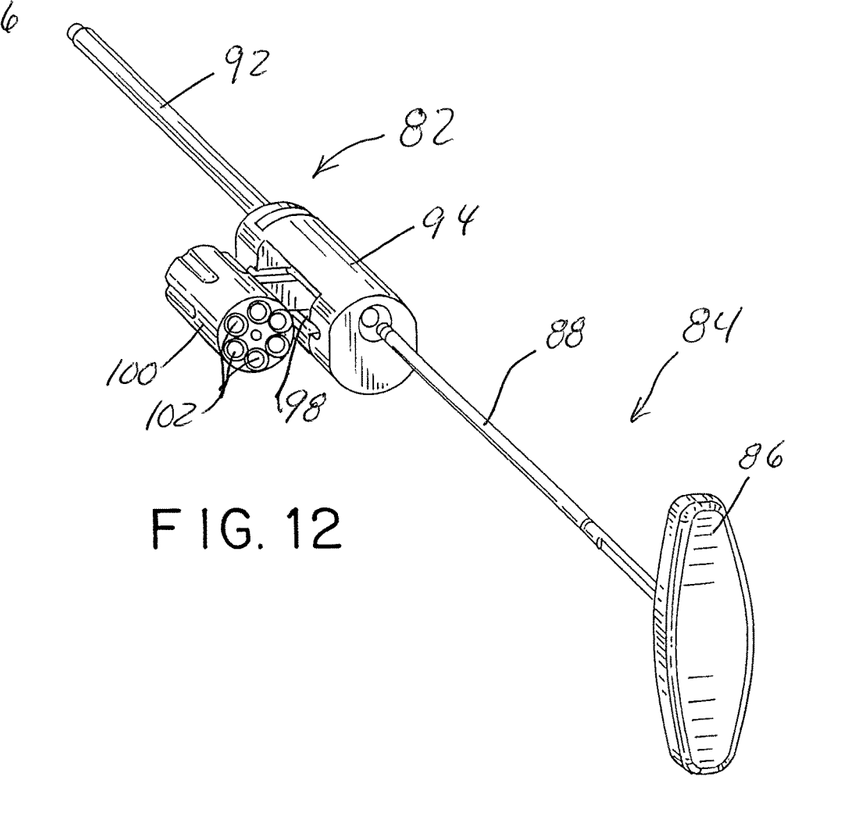
FIG. 12 is a perspective of the graft material injector device of FIG. 11 with components in different operative positions.

FIG. 12 shows the assembly 80 in a loading position with the pusher retracted to a position where the pusher rod 88 is proximal of the side loading aperture 98. This permits the magazine 100 to be inserted into the side loading aperture 98 without interference from the pusher rod 88.

Figures 13, 14:
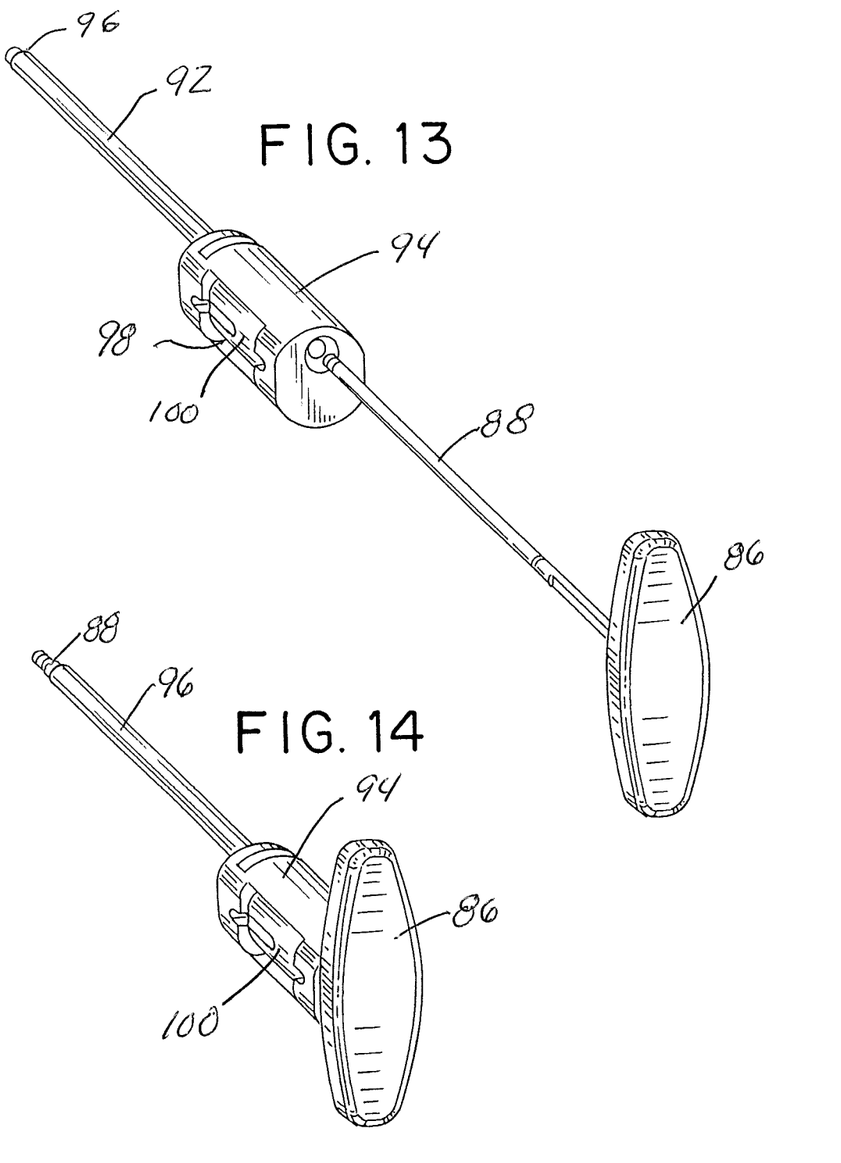
FIG. 13 is a perspective view of the graft material injector device of FIG. 12, with components in different operative positions.
FIG. 14 is a perspective view of the graft material injection device of FIG. 11 taken from a different angle.
Figure 15:
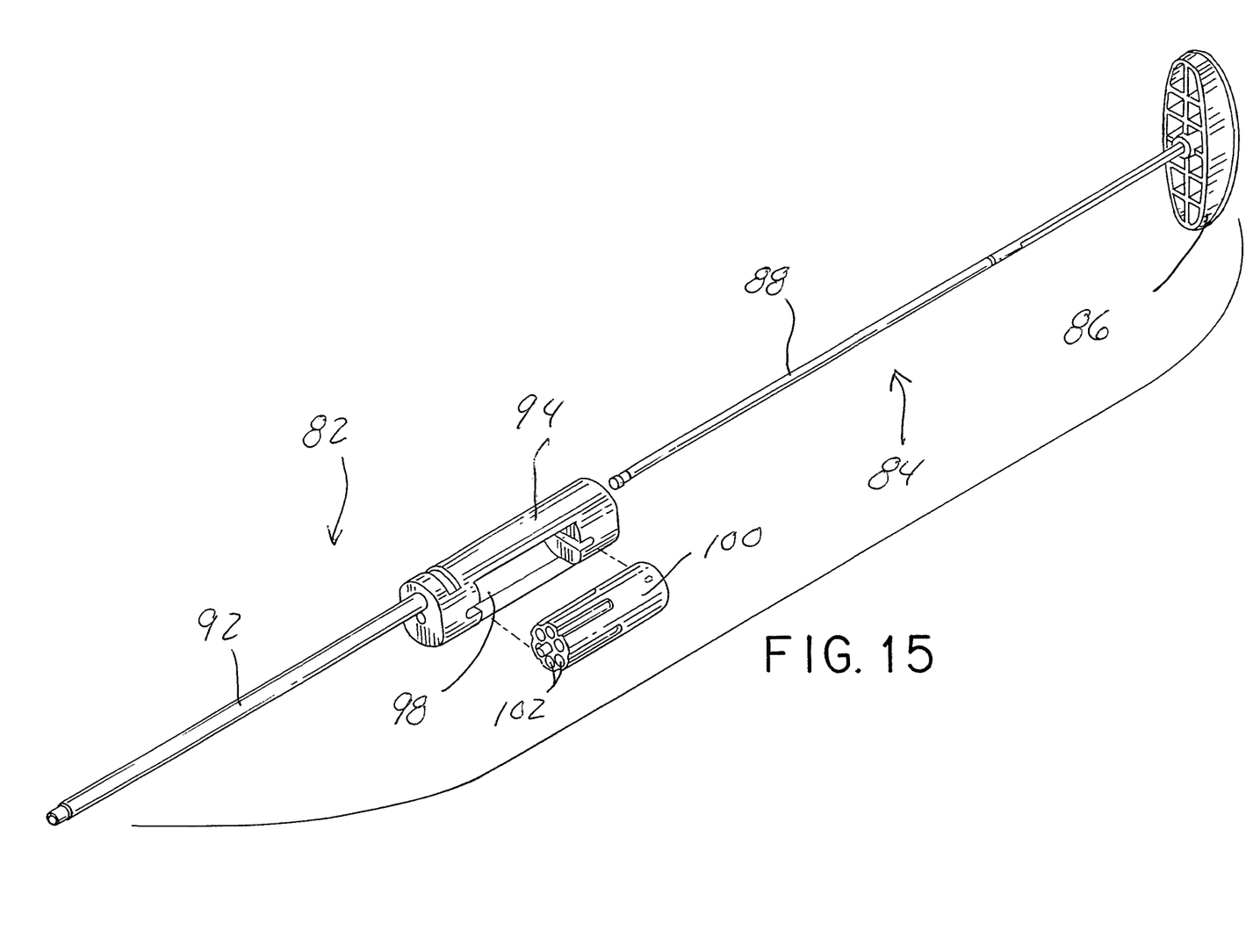
FIG. 15 is a perspective of the graft material injection device of FIG. 11 with components in different operative positions.

FIG. 13 shows a position where the magazine 100 has been inserted in the side loading aperture 98 and the pusher is positioned for insertion into proximal opening 104 in handle 94. FIG. 14 illustrates the pusher fully advanced through the handle, magazine and injector tube and extending beyond the distal end opening 96 of the injector tube. FIG. 15 illustrates a more fully exploded view of the injector assembly 80, with the magazine 100 completely removed from the side loading aperture 98.

Although the present disclosure is described in light of the illustrated embodiments, it is understood that this for the purposes illustration and not limitation. Other applications, modifications or use of the support or distraction device may be made without departing for the scope of this invention, as set forth in the claims now or hereafter filed.

The invention claimed is:
1. A graft material injector comprising:
an injector device including an elongated injector tube, an internal injector tube lumen extending through the injector tube and having a longitudinal axis, a distal injection aperture communicating with the lumen and a side loading aperture for receiving a quantity of graft material into axial alignment with the lumen axis; and
a graft material loader cooperatively engageable with the side loading aperture and adapted to load a selected quantity of graft material into axial alignment with the axis of the injector tube lumen;
wherein the side loading aperture comprises an elongated slot in the injector tube proximal to the injection aperture.
2. The injector of claim 1 wherein the graft material loader comprises a magazine comprising a plurality of graft material chambers, the magazine being operably associated with the injector device to allow sequential placement of each graft material chamber into axial alignment with the injector tube lumen.

3. The injector of claim 2 wherein the injector device includes a housing secured to a proximal end of the injector tube and adapted to cooperate with the magazine to allow sequential placement of each graft material chamber into axial alignment with the injector tube lumen.

4. The injector of claim 3 wherein the magazine comprises a rotary cylinder comprising a plurality of graft material chambers disposed around the cylinder, the cylinder being rotatably associated with the housing to allow rotation of the cylinder to bring each of the graft material chambers into axial alignment with the injector tube lumen.

5. The injector of claim 1 including a pusher movably receivable within the injector tube lumen for applying force to the graft material to force such material through the injector tube lumen and out the distal injection aperture.

6. A graft material injector device comprising:
   an elongated injector tube including an internal lumen; a distal injection aperture communicating with the injector tube internal lumen and loading aperture communicating with the lumen; and
   a plurality of graft material chambers being operably associated with the injector device to allow sequential placement of each graft material chamber into axial alignment with the injector tube lumen;
   wherein the loading aperture comprises an elongated slot in the injector tube proximal to the injection aperture.

7. The injector of claim 6 including a pusher movably receivable within the lumen for applying force to the graft material to force such material through the injection aperture.

8. The injector of claim 6 wherein the injector device includes a proximal end aperture for receiving a pusher into the injector tube lumen proximal of the loading aperture.

9. The injector of claim 6 further comprising a magazine that includes the plurality of graft material chambers, the magazine being operably associated with the injector device to allow sequential placement of each graft material chamber into axial alignment with the injector tube lumen.

10. The injector of claim 9 wherein the injector device includes a housing secured to a proximal end of the injector tube and adapted to cooperate with the magazine to allow sequential placement of each graft material chamber into axial alignment with the injector tube lumen.

11. The injector of claim 10 wherein the magazine comprises a rotary cylinder comprising the plurality of graft material chambers disposed around the cylinder, the cylinder being rotatably associated with the housing to allow rotation of the cylinder to bring each of the graft material chambers into axial alignment with the injector tube lumen.

12. A method of injecting graft material into a spine disc implant employing the apparatus of claim 1 comprising:
    introducing the graft material loader into the side aperture of the injector device, the graft material loader comprising a magazine including a plurality of graft material chambers wherein each chamber includes an amount of graft material;
    axially aligning a first amount of graft material with the injector tube lumen;
    positioning the distal end of the tube into the desired position with respect to the implant;
    moving a push rod through the lumen, thereby applying force to the first amount of graft material to force it out the injection aperture and into association with the implant;
    axially aligning a second amount of graft material with the injector tube lumen; and
    moving the push rod through the lumen, thereby applying force to the second amount of graft material to force it out the injection aperture and into association with the implant.

* * * * *